(12) United States Patent
Hanson et al.

(10) Patent No.: US 6,422,098 B1
(45) Date of Patent: Jul. 23, 2002

(54) DISSOLUTION SAMPLING APPARATUS

(75) Inventors: Royal A. Hanson, Westlake Village; Bruce E. Renslow, Castaic; Guillermo E. Meneses, Chatsworth; Steven W. Shaw, Thousand Oaks; Robinson C. Russell, North Fork, all of CA (US)

(73) Assignee: Hanson Research Corp., Chatsworth, CA (US)

( * ) Notice: Subject to any disclaimer, the term of this patent is extended or adjusted under 35 U.S.C. 154(b) by 0 days.

(21) Appl. No.: 09/407,700

(22) Filed: Sep. 28, 1999

Related U.S. Application Data

(60) Provisional application No. 60/122,613, filed on Mar. 3, 1999.

(51) Int. Cl.[7] .............................................. G06F 15/46
(52) U.S. Cl. ........................................................ 73/866
(58) Field of Search ........................ 73/863.11, 863.33, 73/864.34, 864.35, 864.81, 866; 250/288

(56) References Cited

U.S. PATENT DOCUMENTS

| | | | | |
|---|---|---|---|---|
| 3,791,221 A | * | 2/1974 | Kirschner et al. ............. 73/866 |
| 3,802,272 A | * | 4/1974 | Bischoff et al. ............... 73/866 |
| 4,548,088 A | * | 10/1985 | Hood, Jr. .................. 73/864.34 |
| 4,879,917 A | * | 11/1989 | Eppelmann et al. .......... 73/866 |
| 4,980,296 A | * | 12/1990 | Trisciani et al. .............. 73/866 |
| 5,639,974 A | * | 6/1997 | Hanson et al. ................ 73/866 |
| 5,816,701 A | * | 10/1998 | Martin et al. ................. 73/866 |

* cited by examiner

Primary Examiner—Robert Raevis
(74) Attorney, Agent, or Firm—Jack C. Munro

(57) ABSTRACT

A dissolution sampling apparatus which automatically extracts aliquots which contain a dissolved drug in solution from a plurality of dissolution containing flasks and tests each aliquot for the amount of drug dissolved within the aliquot. The sampling apparatus can resupply the removed aliquot. back to its source or the aliquot can be discarded as waste with new media being resupplied to the source. A syringe is used to remove the aliquots. A mechanically operated valve could be used with each syringe or a plurality of solenoids instead of the mechanically operated valve.

8 Claims, 17 Drawing Sheets

DISSOLUTION SAMPLING APPARATUS

REFERENCE TO PRIOR APPLICATION

The present application refers to provisional application No. 60/122,613 filed Mar. 3, 1999, by the same inventors and title.

BACKGROUND OF THE INVENTION

1) Field of the Invention

The field of this invention relates to dissolution testing equipment for determining the dissolving rate of drugs encapsulated in the form of a tablet, capsule or caplet, which are commonly known as pills and more particularly to an interfacing piece of equipment to be used as a dissolution sampling apparatus.

2) Description of the Prior Art

Drugs are commonly manufactured in the form of pills. The reason for using pills is that when the drug is swallowed by a human, the drug will be disseminated by the body over a period of time as the pill dissolves. Manufacturers of pills are required by law to determine the precise dissolving characteristics of their pill before it is placed on the market. In order to determine the dissolving characteristics, dissolution test equipment is utilized. Although dissolution test equipment is commonly used in conjunction with drugs designed for human consumption, it is considered to be within the scope of this invention to use it with other animals such as horses, cows, rabbits, cats, dogs, monkeys and so forth.

Every form of dissolution test equipment generally utilizes a plurality of liquid containing flasks called testing vessels. In each flask is to be placed a liquid called media, with this media essentially duplicating the liquid solution that is contained within the stomach of the human body. The precise quantity of the solution is placed within the flask. The pill is then inserted into the flask and the time of the insertion then noted. A mixing paddle is inserted within the flask with mixing at a precise rate then occurring. The mixing procedure is to duplicate the natural turbulence that is created within the stomach of the human. Aliquots are removed from the solution at precise time intervals with these aliquots then being analyzed to determine the amount of drug that has been dissolved within the solution in relation to the time that the pill has been in the solution.

In order to insure that the testing process is accomplished as accurate and quickly as possible, such dissolution testing apparatus, in the past, has been designed as follows:

1. Normally the dissolution testing apparatus would have six or eight flasks. Dissolution testing of the pill is accomplished simultaneously in all six or eight flasks with each flask to receive a pill. The average dissolving rate is then calculated between the flasks.

2. The flasks are placed in a bath with this bath to be maintained at a precise temperature. The temperature level is to essentially duplicate the temperature of the stomach liquid within the human.

In the past, the procedure in conjunction with the six or eight flasks is for the technician to remove the media from each individual flask and place it within a collecting vessel. A precise quantity of the media is to be removed and placed within the vessel. At times, it is then required to replace that precise same quantity of raw media back into the flask from which the media has been removed. Also, at other times the media that is being tested is to be reinserted back into the flask. Previously, this tedious procedure of removal of aliquots and replacement of the aliquots or media back into the flask has all been accomplished manually. Inherently, inaccuracies develop. Also because of the time it takes to complete the manual removal procedure, additional inaccuracies develop because what is being calculated is the amount of dissolution of drug within the media within a certain period of time and the removal and replacement procedure takes. time which affects the accuracy of the readings.

SUMMARY OF THE INVENTION

The dissolution sampling apparatus of the present invention is designed to automatically extract samples (aliquots) from multiple flasks that contain media and deposit these aliquots within collecting vials with each aliquot being deposited in a separate collecting vial. The sampling apparatus of this invention can also resupply the aliquot that has been removed back to the flask from which the sample has been taken or the sample can actually be discarded as waste. When discarded as waste, an additional quantity of the raw media liquid can be resupplied to the flask from which the sample has been taken. The present invention is to be used in conjunction with a dissolution test apparatus such is as shown and described within U.S. Pat. No. 5,639,974 which issued on Jun. 17, 1997. However, the present invention can be effectively interfaced with numerous other types of dissolution test apparatus and it is not intended to be solely used with the dissolution test apparatus of the aforementioned patent. However, all dissolution test apparatuses use a multitude, usually six to eight in number, of flasks with the media that is to be removed from each of these flasks. Within each flask is deposited a pill and the flask will normally include a mixing device which is to be used to create a turbulent action within each flask essentially duplicating the. turbulent action that is naturally created within the human stomach. The definition of pill is to also include capsules and caplets or any type of device which is to dissolve.

The present invention can comprise two different models with both models utilizing a plurality of piston operating devices which we refer to as syringes. There is to be a syringe for each vessel that contains media. Each syringe includes a body that is basically hollow within which is mounted a piston. This piston is retractable and expandable within the body. This retraction and expansion is accomplished by means of a motor which is precisely controlled by software. Associated with each syringe are a plurality of valves. Each valve is also operated by the software as to whether the valve is opened or closed. The first model is referred to as the DISSOSCAN and the-second model is referred to as the MAXIMIZER. The DISSOSCAN utilizes a single three-way solenoid valve that are mounted in conjunction with each syringe. The MAXIMIZER utilizes four two-way solenoid valves operated to accomplish the valving in conjunction with each syringe. The MAXIMIZER model is designed to be more versatile than the DISSOSCAN model with the MAXIMIZER able to perform a greater number of functions. However, the MAXIMIZER model has a disadvantage in that it is inherently more expensive.

DETAILED DESCRIPTION OF THE PREFERRED EMBODIMENTS

Figure 1:
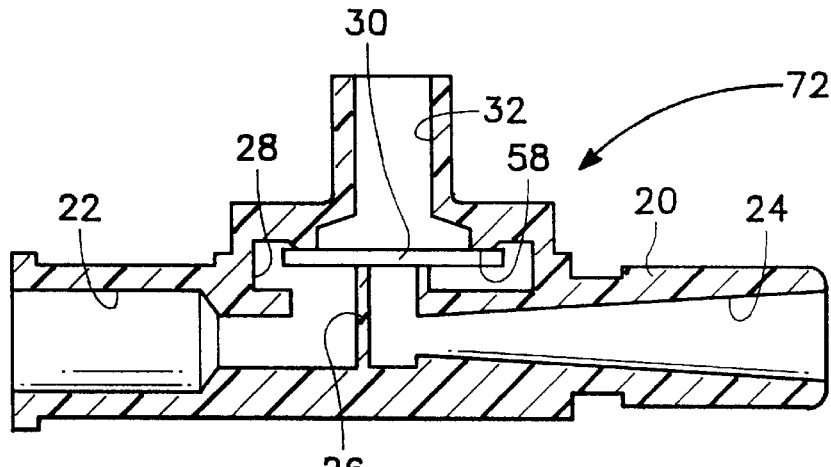
FIG. 1 is an enlarged cross-sectional view of the dual check valve that is used in conjunction with the DISSOSCAN model of dissolution sampling apparatus of the present invention showing the valve in the non-flow position.
Figure 2:
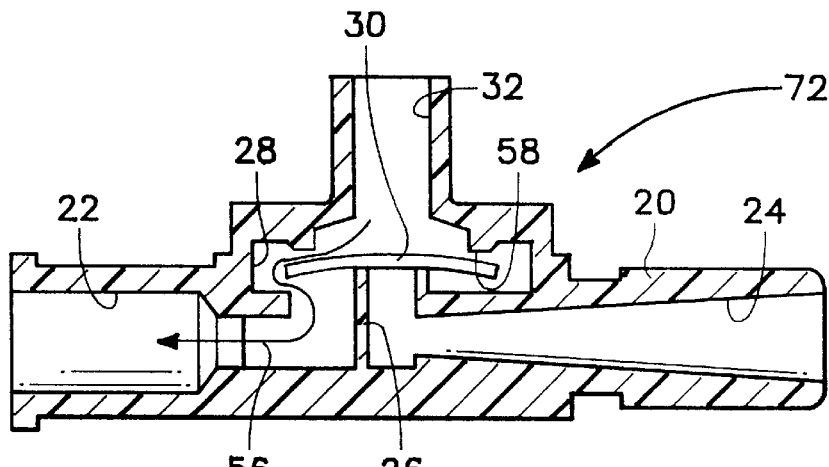
FIG. 2 is a cross-sectional. view similar to FIG. 1 but showing the intake flow direction of the valve.
Figure 3:
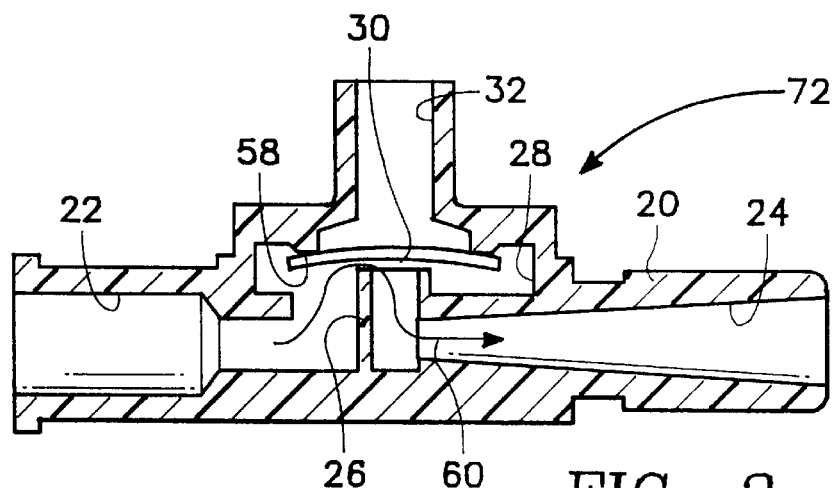
FIG. 3 is an enlarged view similar to FIG. 2 but showing the exit or outflow mode of direction of flow through the valve.

FIGS. 1–3 schematically show the dual check valve 72 that is utilized in conjunction with the DISSOSCAN model. The dual check valve 72 has an elongated housing 20 which includes an intake or second port 22 and an outlet or third port 24. Separating the port 22 and the port 24 is a wall 26. The wall 26 connects with a chamber 28. Within the chamber 28 there is mounted a silicon disc which will be referred to as a diaphragm 30. Connecting with the chamber 2.8 is a first port 32. Port 32 is to be connected with a reservoir such as flask 34 shown in FIG. 4. The-port 22 is connected through tube 36 to a syringe chamber 38 located within syringe body 40. Movably mounted within the syringe chamber 38 is a piston 42. Piston 42 is connected to rod 44 which in turn is mounted to an arm 46. The arm 46 is mounted on lead screw 48. The lead screw 48 is movable in the up direction as indicated by arrow 51 and down in the direction as indicated by arrow 50 by means of a motor 52.

FIG. 1 is a representation of the actual construction of the valve 72 shown in FIGS. 1–3. The diaphragm 30 is shown in FIG. 1 closing of ports 24 and 32 so no media can pass through the valve 72. Referring particularly to FIG. 2, when the piston 42 is moved in a retracted or down direction, which is in the direction of arrow 50, media is caused to flow from the flask 34, through tube 54, through port 32, around the silicon disc 30, into port 22 and into the syringe chamber 38. The direction of this flow is indicated by arrow 56. When the desired precise quantity of media has been contained within the port 22 and syringe chamber 38, the syringe motor 52 is activated which rotates the lead screw 48.in an opposite direction which will be the up direction as shown by arrow 51. This results in the piston 42 moving of the media contained within the chamber 38 and the port 22 to be pressed against the silicon disc 30 forcing the disc 30 tightly against seat 58, which is clearly shown in FIG. 3 of the drawings. This permits the flow of media from port 22 directly into port 24. This direction of flow is indicated by arrow 60. This means that the media is to flow through tube 62 and then through a spectrophotometer 64. Such spectrophotometers are well known in the field and function to immediately calculate the percentage of drug concentration within the liquid flowing through the spectrophotometer 64. One manufacturer of spectrophotometers is Hewlett-Packard Corporation.

Figure 4:
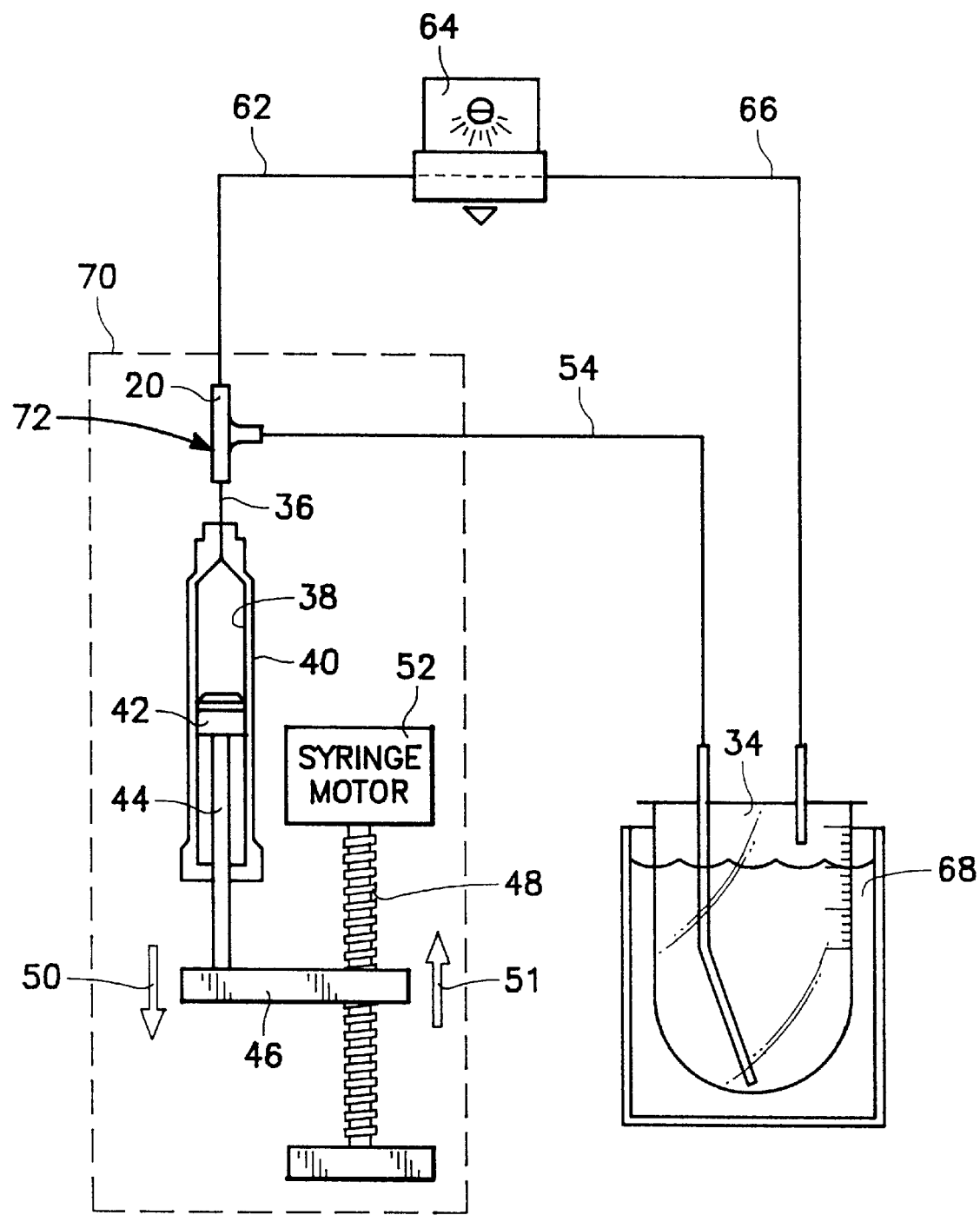
FIGS. 4–18 schematically show different modes of operation of the two models of dissolution test sampling aparatus of the present invention.

From the spectrophotometer 64 the liquid is to flow through tube 66 back into the flask 34. FIG. 4 relates only to the DISSOSCAN model that can be utilized with only one bath 68 within which will normally be mounted somewhere in the range of six to eight of the flasks 34. The bath 68 is to comprise a quantity of a liquid (usually water) that is maintained at a preset temperature. The flasks 34 are to be submerged in the bath 68 with the open top of the flasks 34 locate above the surface of the liquid in the bath 68 so none of the liquid can enter the flask 34. The liquid in the bath 68 is to maintain the media in the flasks 34 at the preset temperature. For each flask 34 there is to be a separate syringe body 40 and piston 42. The removal of the aliquots, or samples, from each of the flasks 34 is to be accomplished simultaneously with the flow through the spectrophotometer 64. It is to be understood that the spectrophotometer 64 is deemed to be a conventional, commercially available apparatus which can be purchased from numerous sources not only from Hewlett-Packard Corporation.

Basically, the configuration shown in FIG. 4 utilizes one bath 68, one sampling apparatus 70, which includes multiple numbers of the syringe bodies 40 with their being a syringe body 40 for each flask 34 located within the bath 68. There is utilized a detection apparatus in the form of a spectrophotometer 64 with the media that is removed from the flask 34 to be redeposited back into its same flask 34 from which it is removed. The media from the tube 36 is transmitted through the dual valve 72 which is the valve that was previously discussed in relation to FIGS. 1–3. Other types of valves could be used instead of the dual check valve 72. One example is a 3-way solenoid valve.

Referring to FIG. 5, there is again shown the DISSOSCAN embodiment which utilizes one bath 68 and one sampling apparatus 70 with a multiple number of the syringe bodies 40 and pistons 42. The difference in FIG. 5 when compared to FIG. 4 is that instead of returning the aliquot within the flask 34 by tube 62, with it being understood there is a separate tube 62 for each syringe body 40, the aliquots are deposited within a collector module 74. The collector module 74 is deemed to be conventional and is commercially available as from Zymack Corporation of Hopkinton, Massachusetts. The collector module 74 includes a plurality of deposit vials 76. Within each deposit vial 76 there is to be deposited an aliquot. One syringe body 40 connects with deposit vial 76 that is numbered 1 and 6. Second syringe body 40 connects with a separate deposit vial 76 that is numbered 2 and so forth with each deposit vial 76 connecting with a separate syringe body 40. The collector module 74 functions as an interim storage device to assemble and collate aliquots according to time collected with each deposit vial to then be removed and analyzed. The aliquot is then moved to a return vial 78. Again, there is a return vial 78 for each deposit vial 76. From the return vial 78 the aliquot is cause to flow through tube 80 back to be redeposited into its flask 34.

Figure 5:
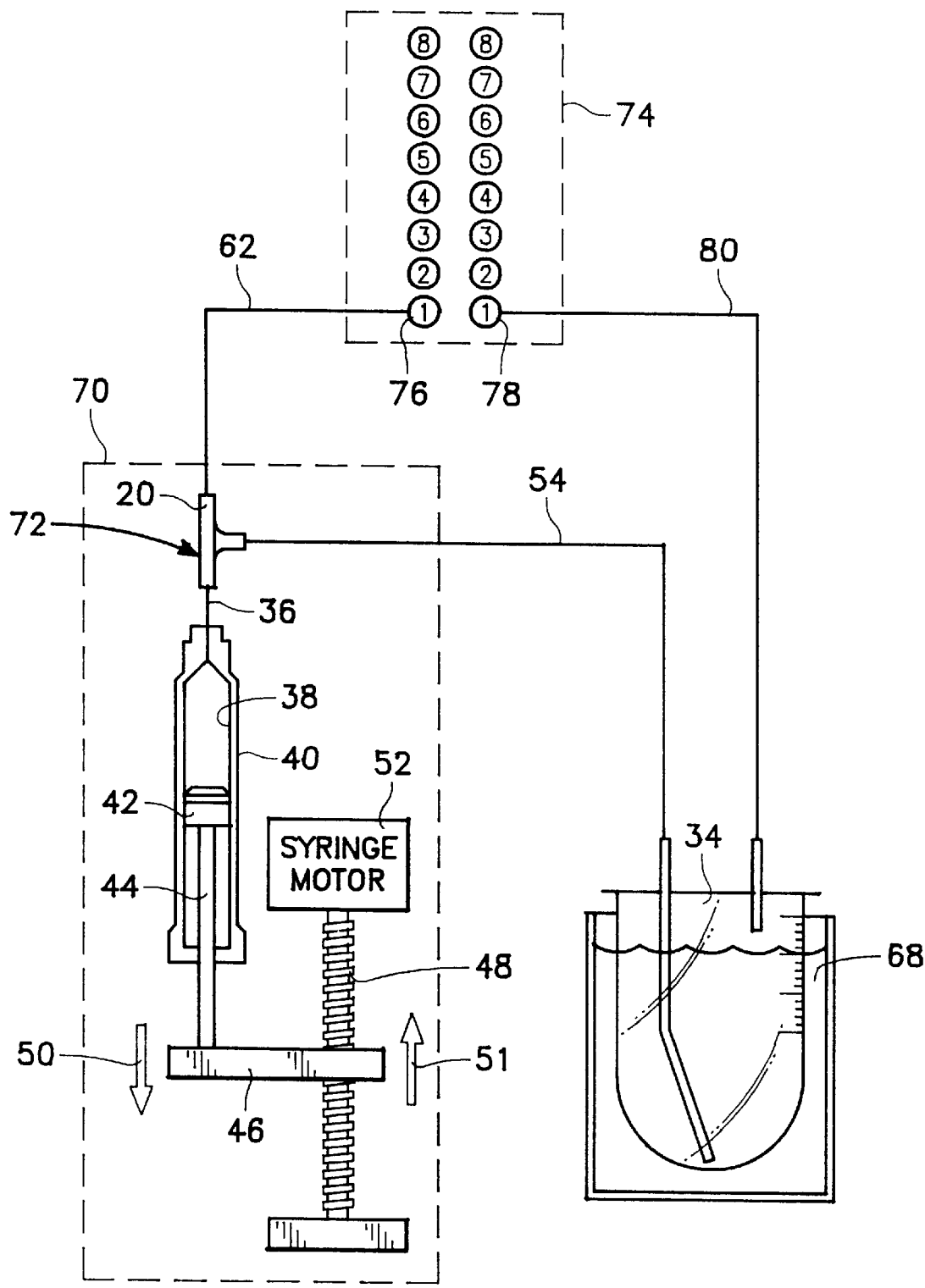
Figure 6:
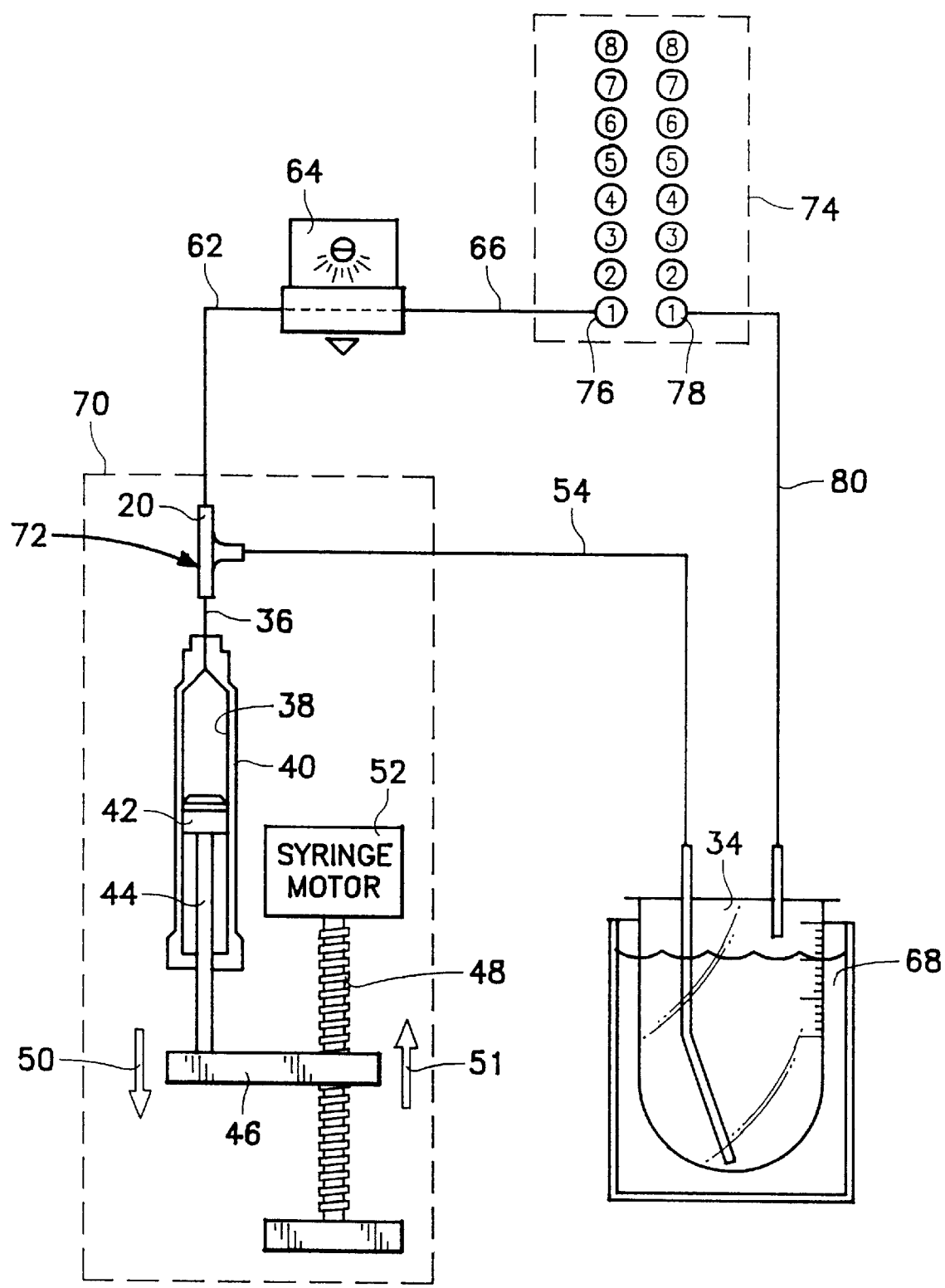

Referring particularly to FIG. 6, there is again shown the DISSOSCAN embodiment with like numerals being employed to refer to like parts. The only difference between FIGS. 5 and 6 is that there is included within fluid conducting tube 62 a spectrophotometer 64. The analyzed results from the aliquot collected in the collector module 74 can be used to compare with the results from the spectrophotometer 64.

Reference now is to be had to FIGS. 7–18 which is directed to the different configurations of the MAXIMIZER embodiment of this invention. Again, similar numerals have been utilized to refer to similar parts. There again, is utilized at least the single bath 68 and a multitude of flasks 34. For each flask 34 there is a separate syringe body 40 and a separate syringe piston 42. Flow of media into and out of the syringe body 40 is now controlled by four separate solenoids 82, 84, 86 and 88 which are mounted on a solenoid housing. However, in the. configurations shown in FIGS. 7–9, the solenoids 84 and 86 are not operated. These solenoids 82, 84, 86 and 88 are controlled electronically by software which is supplied with the sampling apparatus of this invention.

Figure 7:
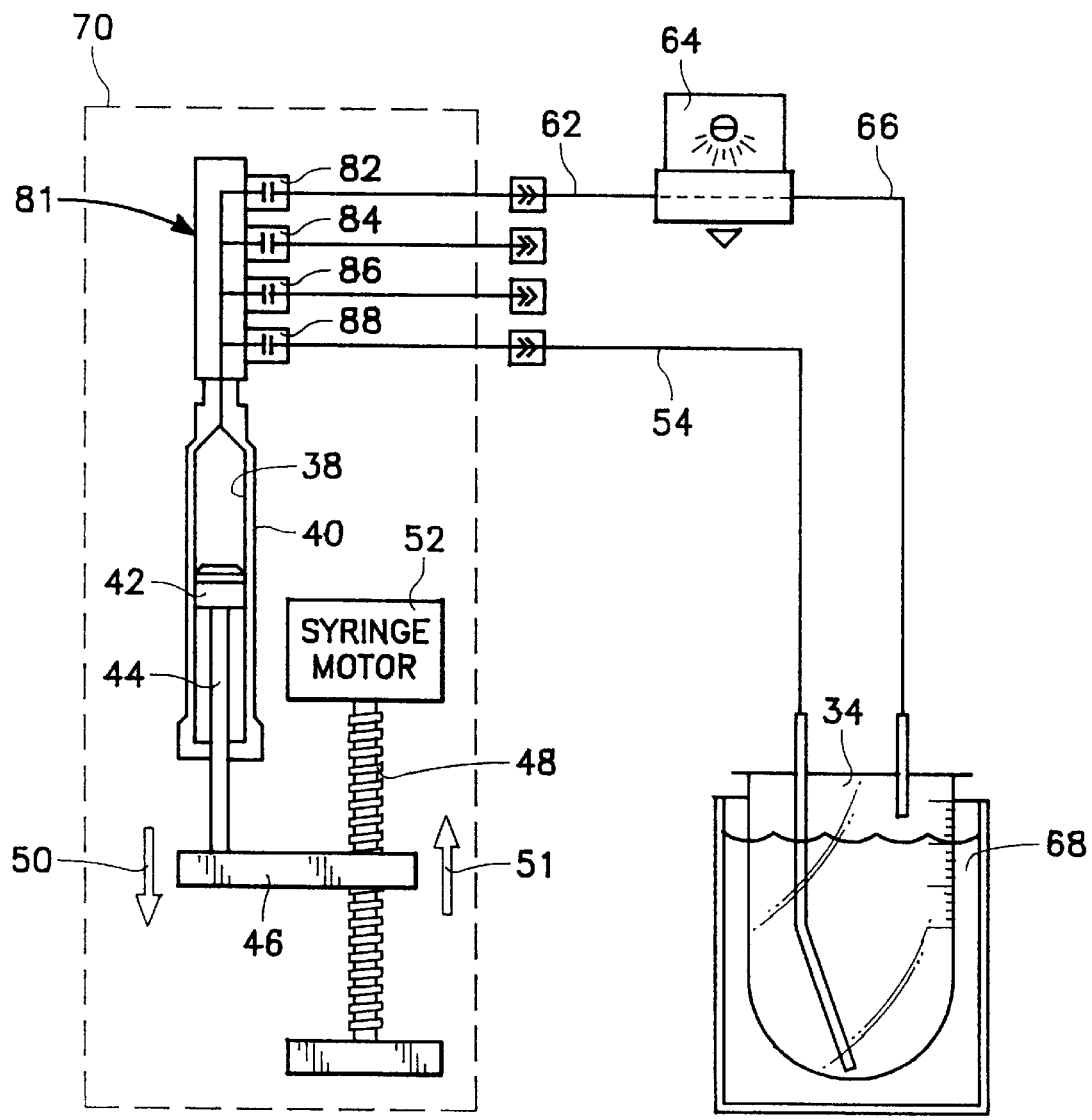

Solenoid 88 controls the flow of media from flask 34 through tube 54 to syringe body 40. Solenoid 82 controls the flow of media through outflow tube 62 to the spectrophotometer 64 and then hence through the tube 66 back to the flask 34. The configuration in FIG. 7 is to detect the percentage of drug being dissolved within the media contained within each flask 34 by means of a spectrophotometer 64 which is similar to FIG. 4.

Figure 8:
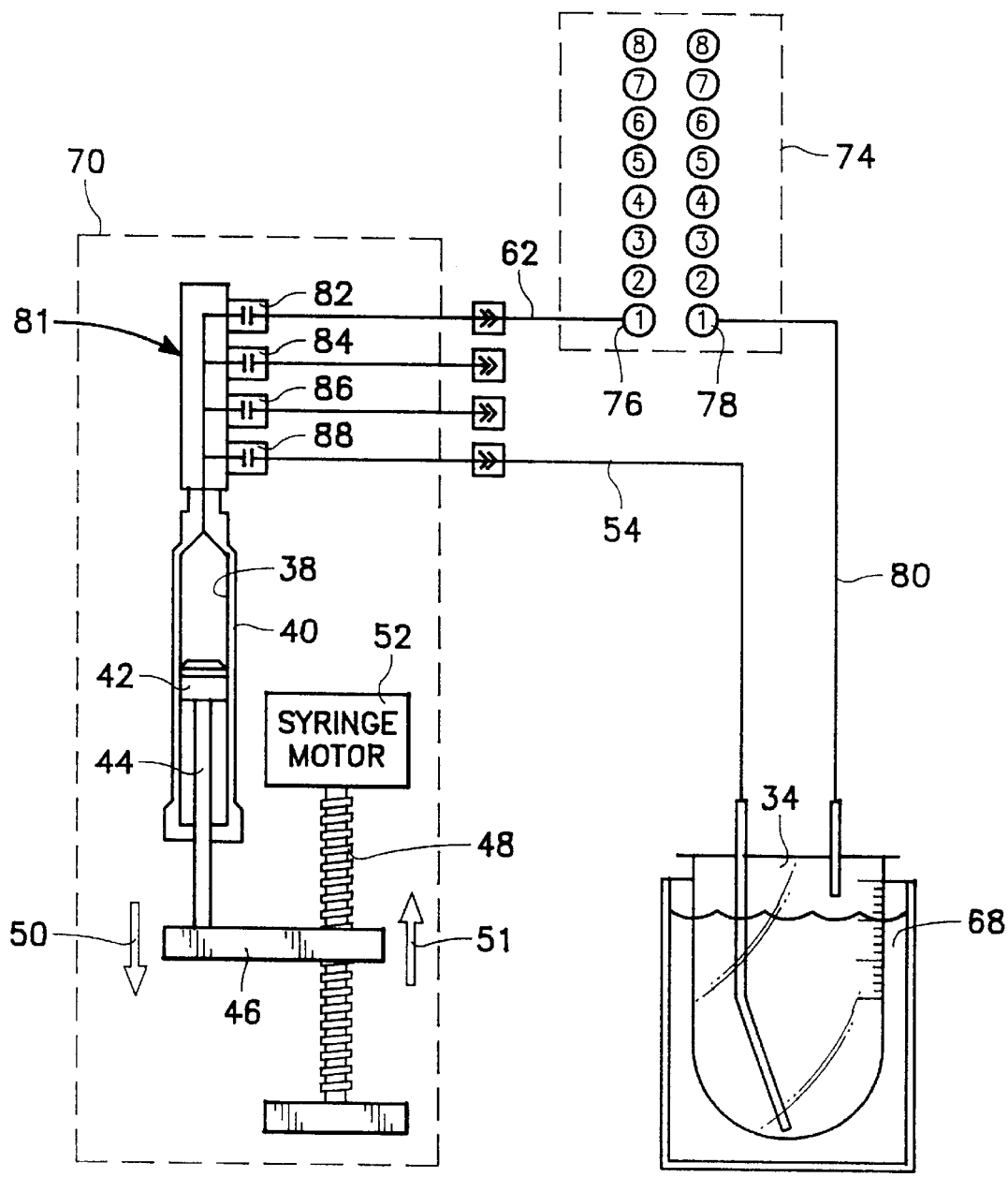

Referring particularly to FIG. 8, there is shown a configuration wherein the media is supplied to a collector module 74. Basically, the version shown in FIG. 8 will operate in a manner similar to FIG. 5.

Figure 9:
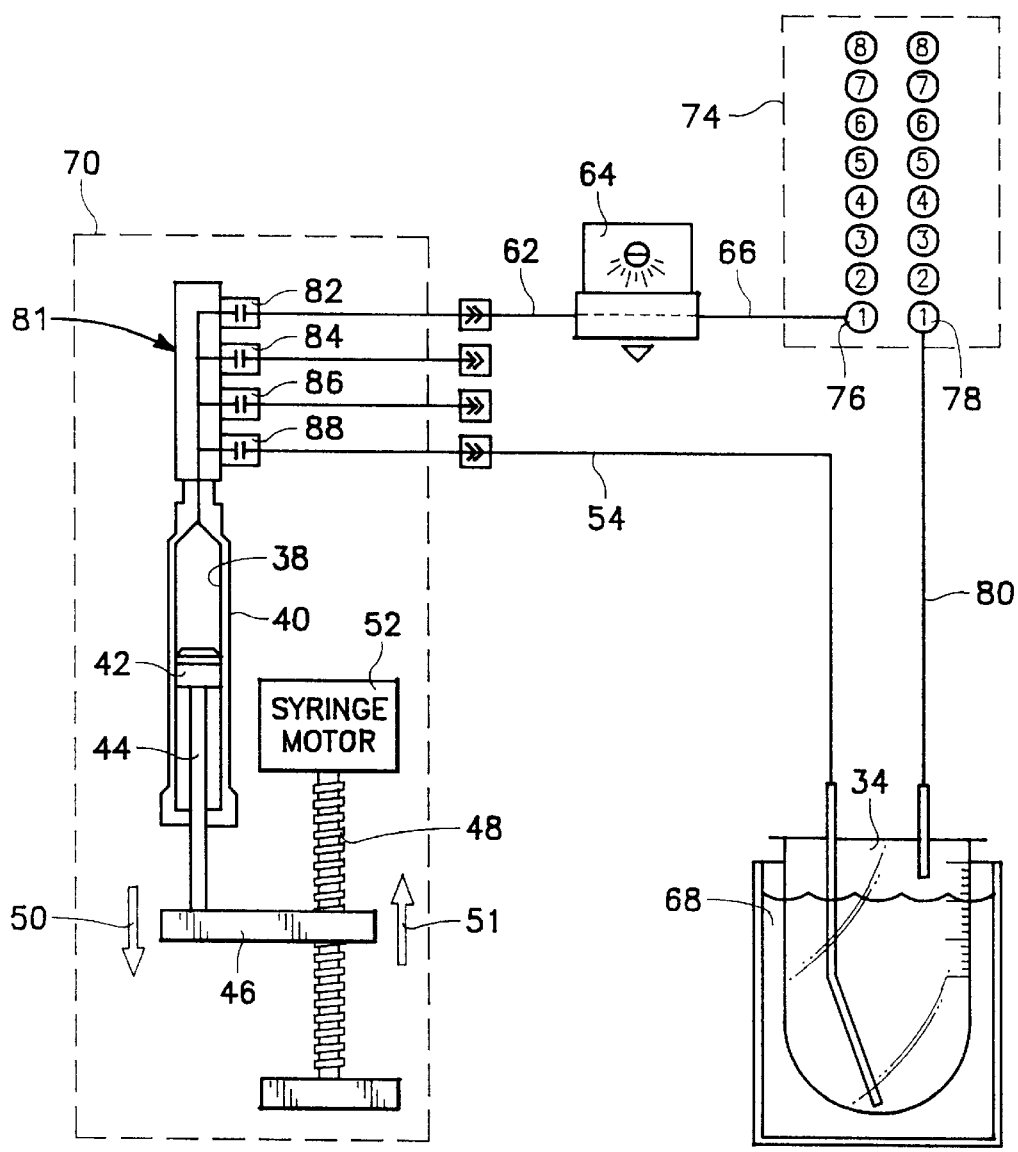

The configuration shown in FIG. 9 is basically similar to FIG. 8 with the addition of the spectrophotometer 64. The configuration of FIG. 9 is basically similar to the configuration of FIG. 6.

Figure 10:
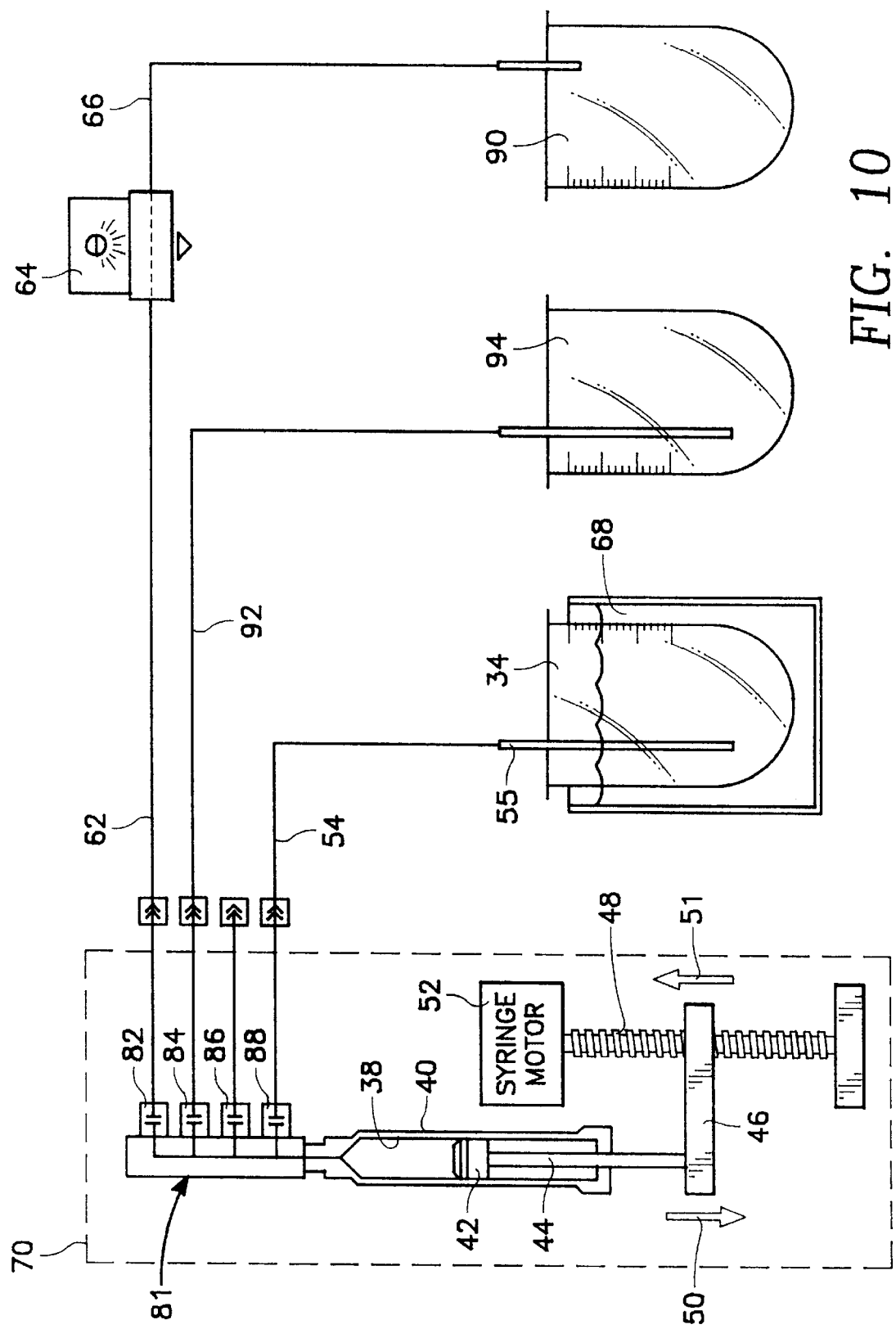

Referring particularly to FIG. 10, there is a MAXIMIZER configuration which is basically similar to that shown in FIG. 9 except that there is no collector module and there is utilized instead a waste flask 90. Generally there will be only one waste flask 90 for all of the flasks 34. Solenoid 84 is connected by tube 92 to a media replace flask 94. Again, there will only be one media replace flask 94 for the series of flasks 34. The user with the configuration of FIG. 10 has the option to load the syringes 40 with fresh media from flask 94 to replenish the flask 34. If small volume aliquots are being taken, there may not be a need for a media replace flask. However, if large volume aliquots are being drawn, the volume of the media that remains after three or four aliquots are drawn is so low that saturation is approached of the remaining media in each flask by the dissolving pill. Saturation produces inaccurate results. To avoid saturation, a quantity of new media is introduced to the flask identical in volume to the aliquot immediately after its removal. Also, the media contained within flask 94 could be utilized to clean the tubes 62 and 66 as well as the internal chamber of the syringe 40 and deposit that within the waste flask 90. Also, the solenoid 88 connects through tube 54 to probe 55. When solenoid 88 is actuated, media is to be drawn within probe 55 and into tube 54 and into syringe chamber,38.

Figure 11:
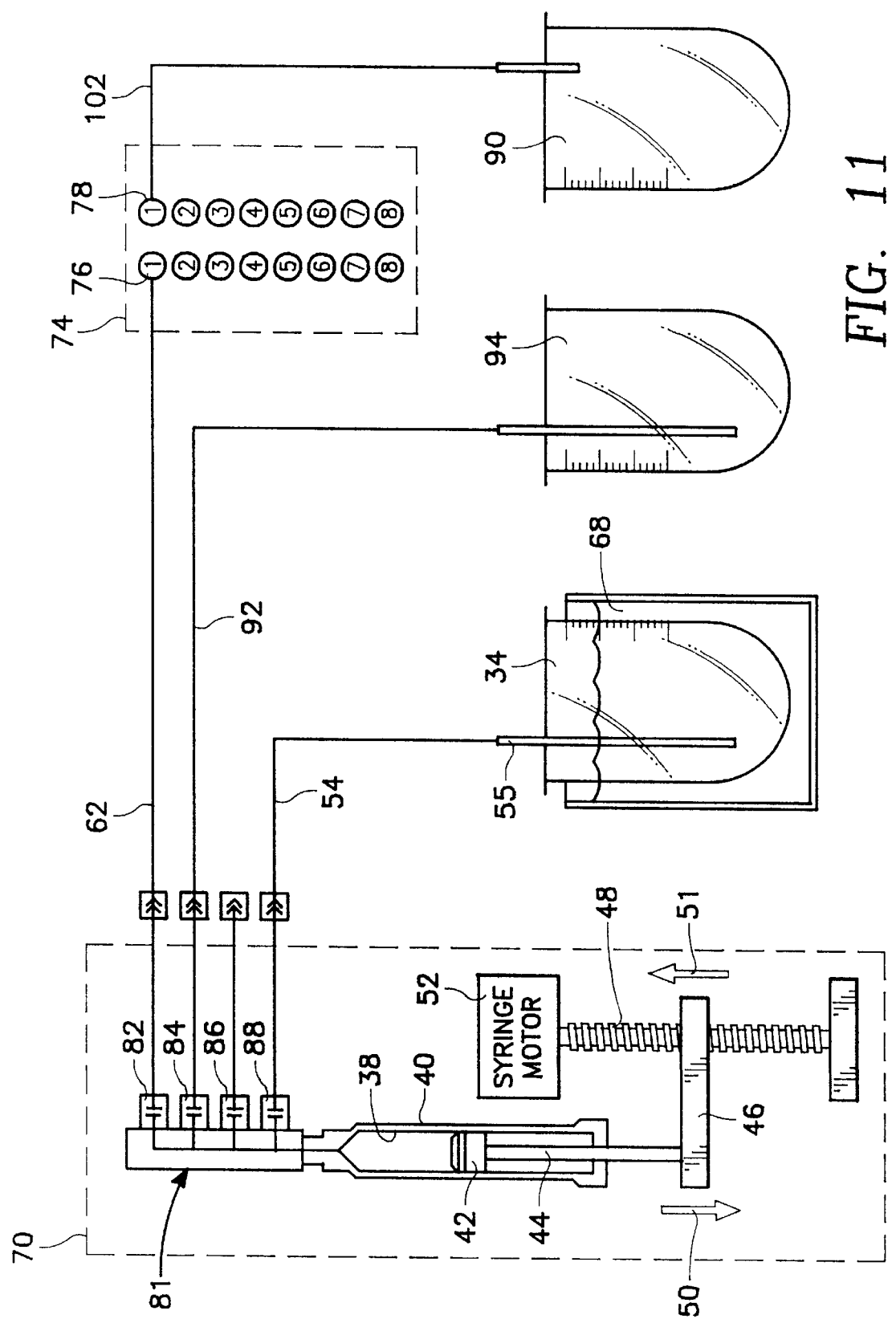

The configuration shown in FIG. 11 is basically similar to that shown in FIG. 10 with the exception that the tube 62 connects to collector module 74 and from vials 78 of module 74 the media is to be deposited within waste flask 90. Replacement media in media replace flask 94 may be utilized as diluent and added to collected samples in collector 74 to achieve dilution.

The configuration shown in FIG. 12 is again for the MAXIMIZER and is the same as in FIG. 11 with the addition of the spectrophotometer 64 within the fluid conducting tube 62. From the spectrophotometer 64 there is a fluid conducting tube 66 for each syringe body 40 each of which connects to a separate vial 76 of the collector module 74.

Figure 12:
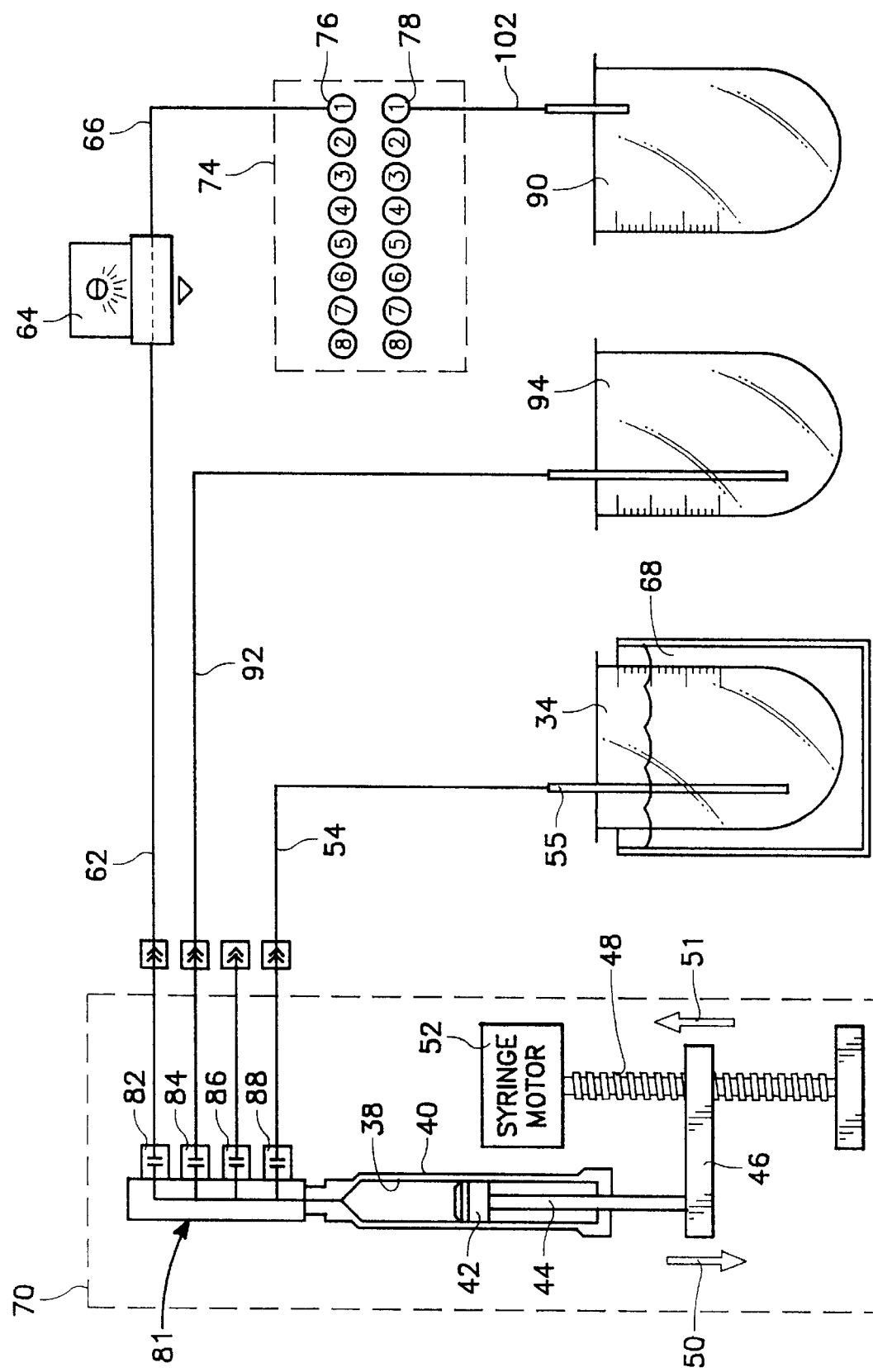
Figure 13:
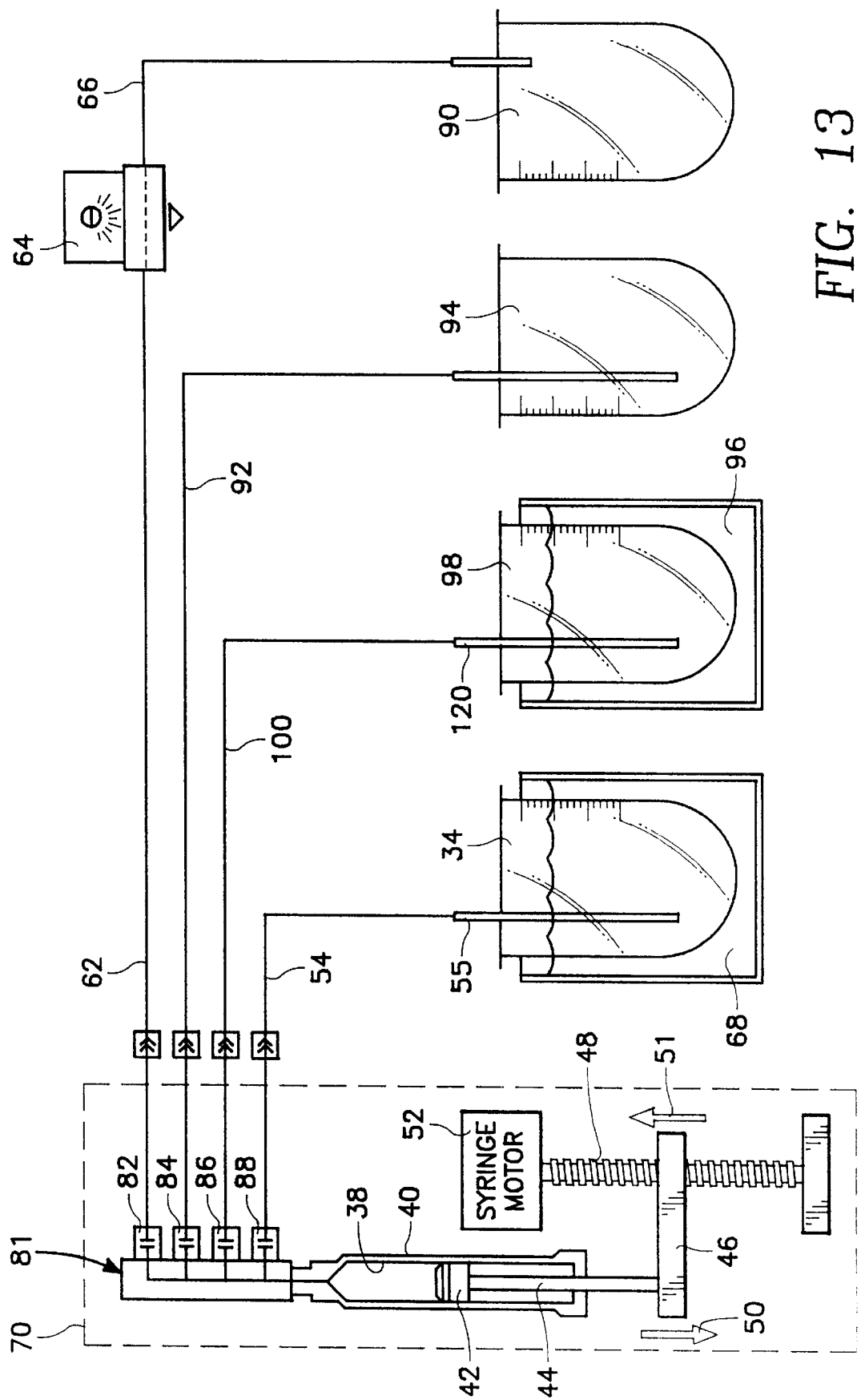

Referring particular to FIG. 13 there is shown a configuration which is again basically similar to FIG. 12 except there is no collector module 74 and, instead of utilizing a single bath 68, there is a second bath 96. Included within the second bath 96 are a plurality of flasks 98. It is to be understood that there will be a plurality of such flasks 98, such as six or eight in number, in bath 96. Each flask 98 is connected by valves 97 and 99 to a separate tube 100. Valves 97 and 99 are similar to previously described valves 59 and 61. From valve 97 there is a tube 120 that extends to directly adjacent the bottom of flasks 98 for withdrawing of media. Tube 122 extends from valve 99 to within flask 98 directly adjacent the top edge which is used to add media to flask 98. Tube 100 is connected to solenoid 86. As programmed by the user, a sampling sequence can be generated for each of the flasks 34 of the bath 68. After that sampling sequence, there will be a second sampling sequence generated for each flask 98 of the bath 96. Using of this configuration will decrease by half the time it takes to make the analyzations of the drug used in the flasks 98 is the same as in flasks 34 since twice as many aliquots are being withdrawn in the same time period. Also, flasks 98 could contain a different drug so the same apparatus could be used to make two different readings of two different drugs. Again, the user has the option to load the syringes with fresh media from flask 94 and replenish either flasks 34 or flasks 98. Also, the fresh media could be utilized to wash the tubes 62 and 66 prior to being deposited within the waste-flask 90.

Figure 14:
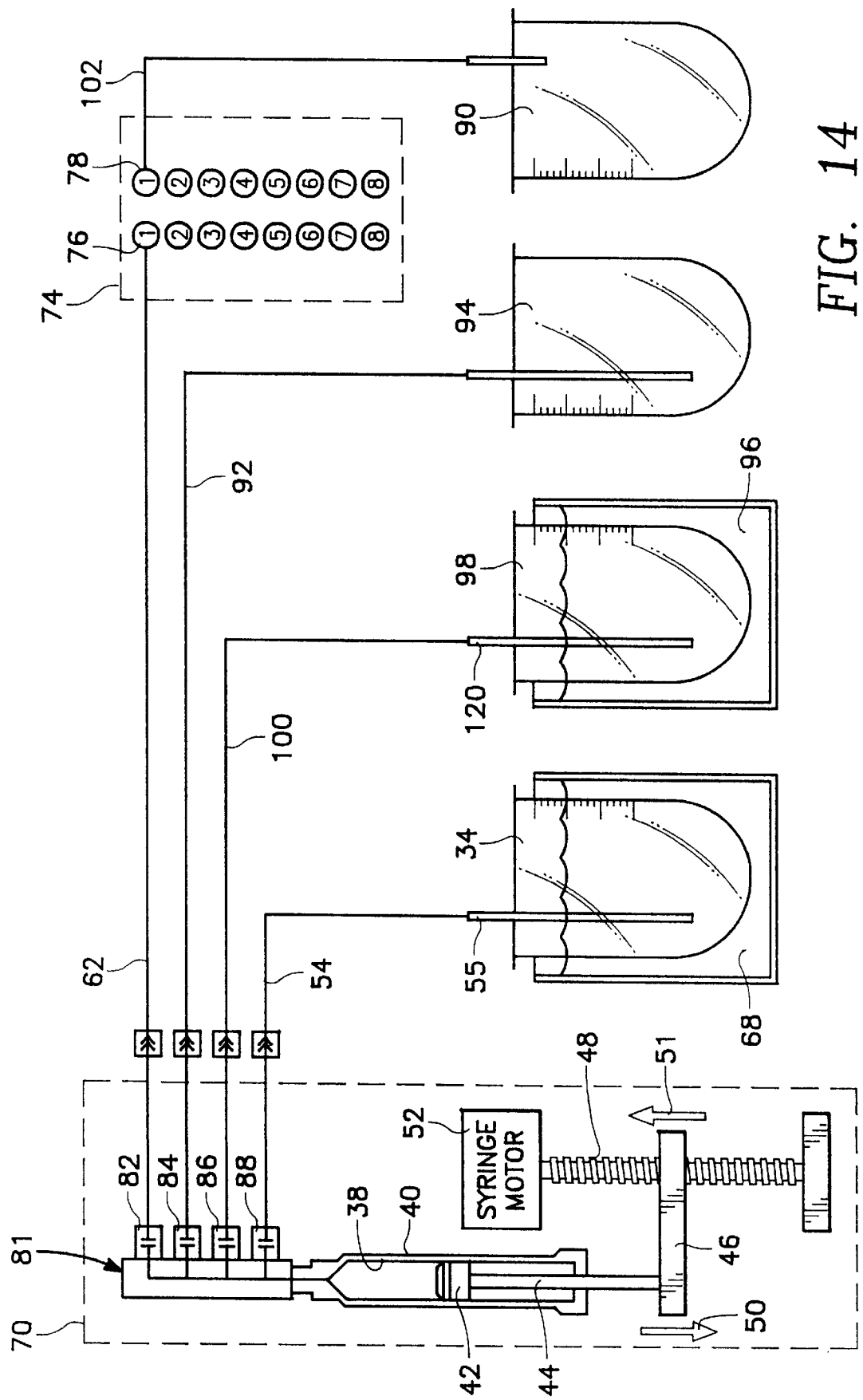

The configuration shown in FIG. 14 is basically similar to FIG. 13 with the addition of the collector module 74 mounted in conjunction with the tubes 62. From each vial 78 of the collector module 74, the media is to be caused to flow through tubes 102 into waste flask 90. There are similar tubes 102 in conjunction with the configurations of FIGS. 11 and 12.

Figure 15:
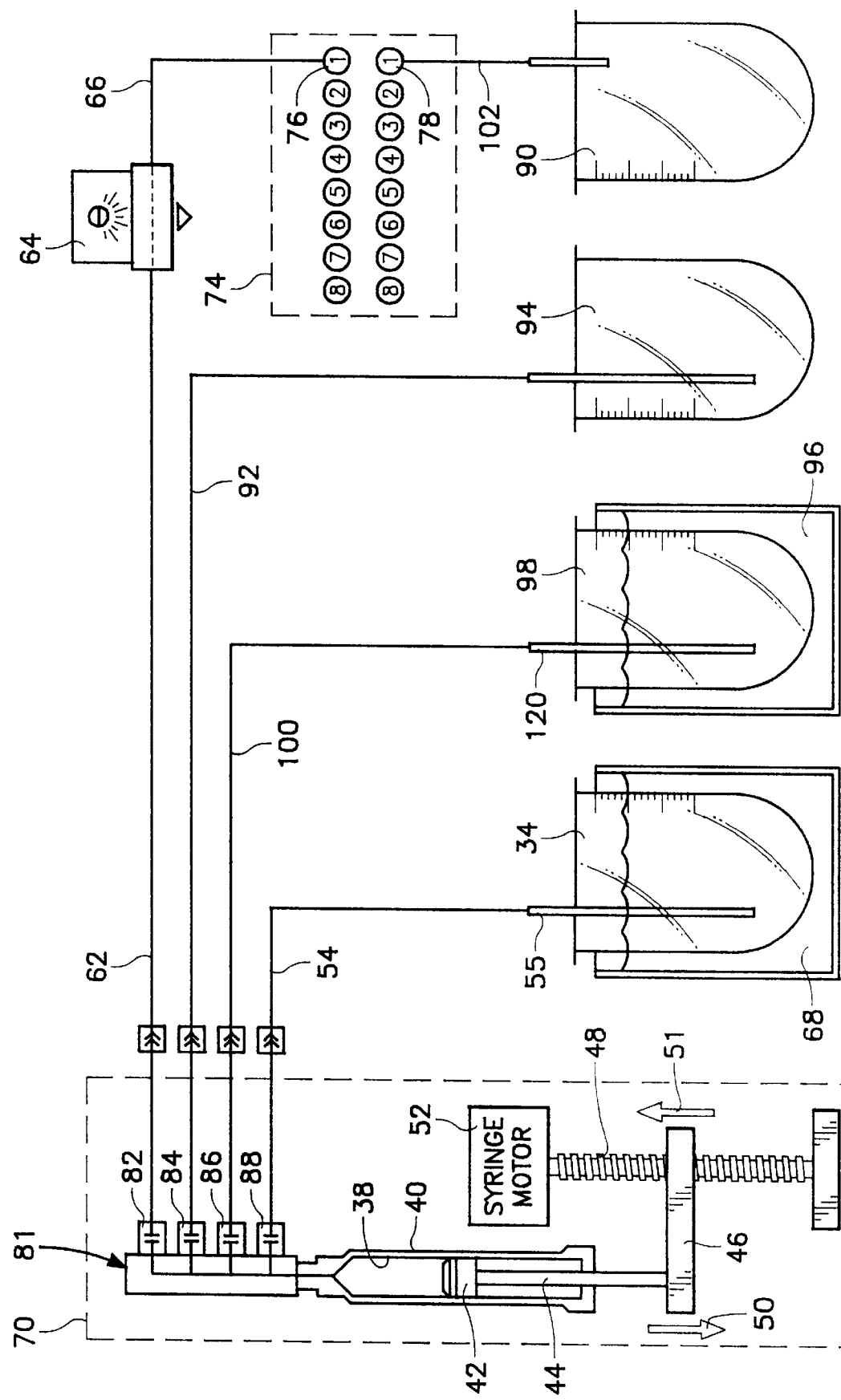

FIG. 15 is basically similar to FIG. 14 with the addition of the spectrophotometer 64 within tube 62. As programmed by the user, a flow cell flow signal is generated to the spectrophotometer 64. A program sampling volume is then collected through tube 66 into the vial 76 of the collector module 74. It is to be understood that the procedure is repeated for both baths 68 and 96. The user has the option to load the syringes 40 with fresh media from flask 94 and then replenish lost media from either bath 34 or 98 or utilize the fresh media to wash the tubes prior to depositing of such within the waste flask 90.

Figure 16:
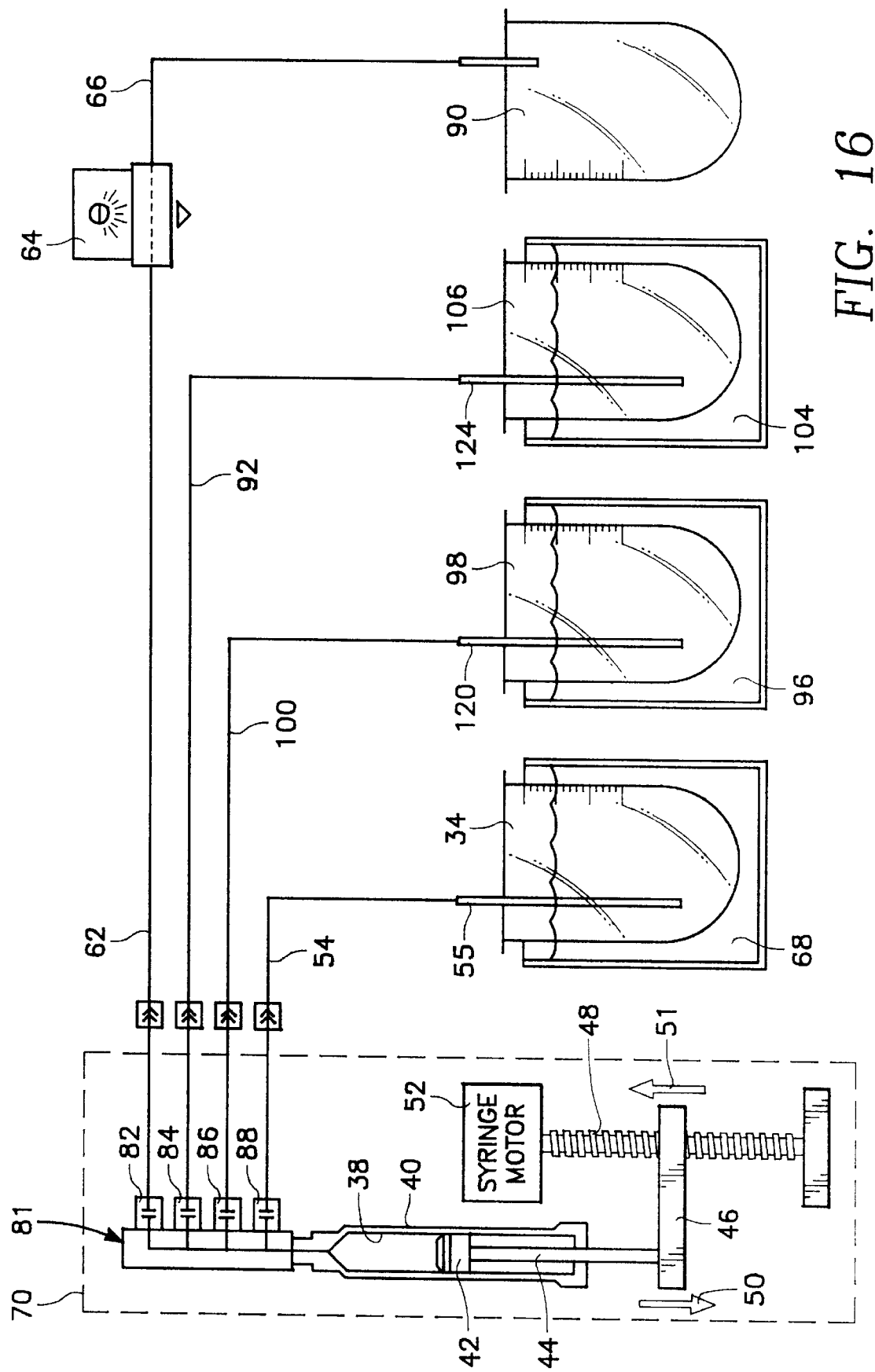

Referring particularly to FIG. 16, an additional bath 104 containing flasks 106 could be used. Valves 103 and 105 connect with tube 92 and solenoid 84. Extending from valve 103 is a tube 124 that extends to directly adjacent the bottom of flask 106 to be used to withdraw media from flasks 106. Extending from valve 105 is a tube 126 that extends just into flask 106 which is to be used to add media to flask 106. Withdrawing media near the bottom of flasks 34, 98 and 106 is preferred so as to only withdraw media that contains the most dissolved drug. Adding media is preferred to occur near the top of flasks 34, 98 and 106 which is spaced from the bottom of the flasks and will normally affect the drug concentration in the flasks. Valves 103 and 105 are similar to valves 59 and 61. Bath 104 could be added to, decrease the time by three that is required to. analyze a drug. Also, using bath 104 could permit three different drugs to be analyzed by the same apparatus. There will normally be the same number of flasks 106 to flasks 34. In operation of the configuration shown in. FIG. 16, the user is to program the sequence to include the bath 106 in sequence with the other baths 96 and 68. Tube 66 connects directly from the spectrophotometer 64 to the waste flask 90.

Figure 17:
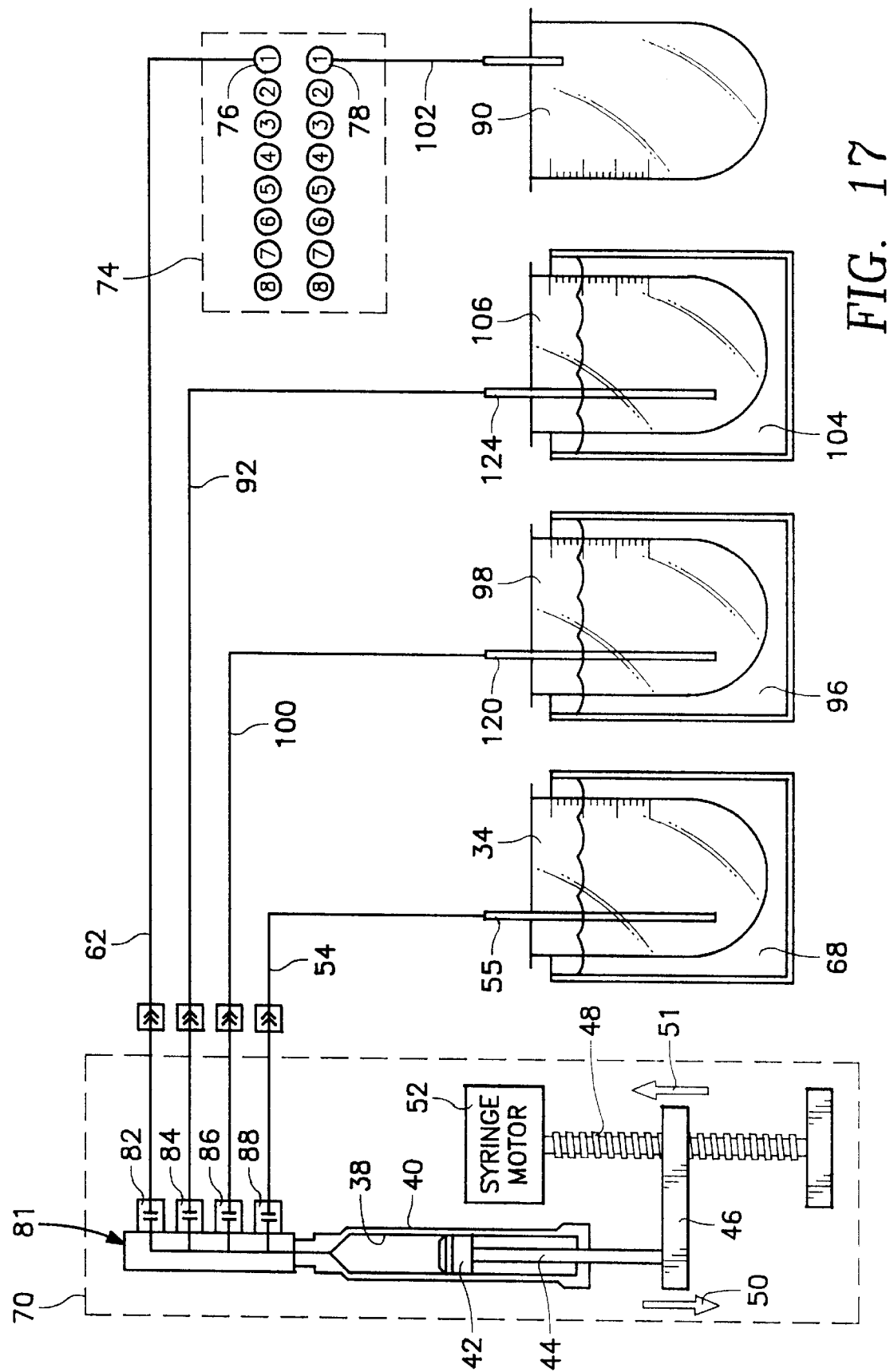

FIG. 17 is a configuration which is again basically similar to FIG. 16 with the exception that instead of using the spectrophotometer 64 there is mounted the collector module 74 between the tubes 62 and 102.

Figure 18:
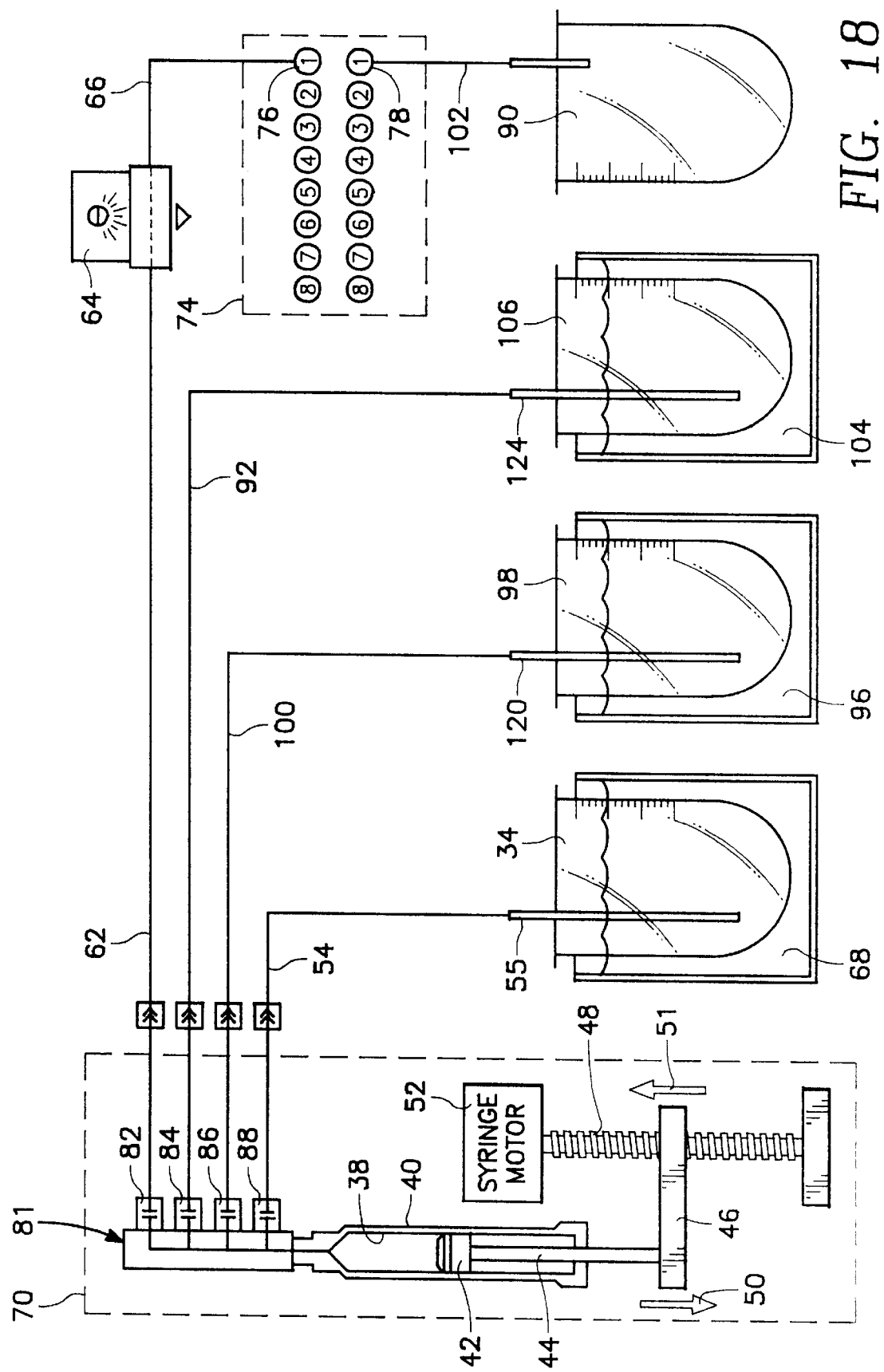

Referring particularly to the configuration shown in FIG. 18, the spectrophotometer 64 is placed within the tubes 62. A program sampling volume is then collected into a collector module 74 after being analyzed by the spectrophotometer 64 for bath 68. Before repeating the procedure on baths 96 and 104, the MAXIMIZER waits for the offset time to elapse. Offset time is the inoperating time between collecting for bath 68 and bath 96, and also bath 96 and bath 104. No replacement media is available with this configuration.

Figure 19:
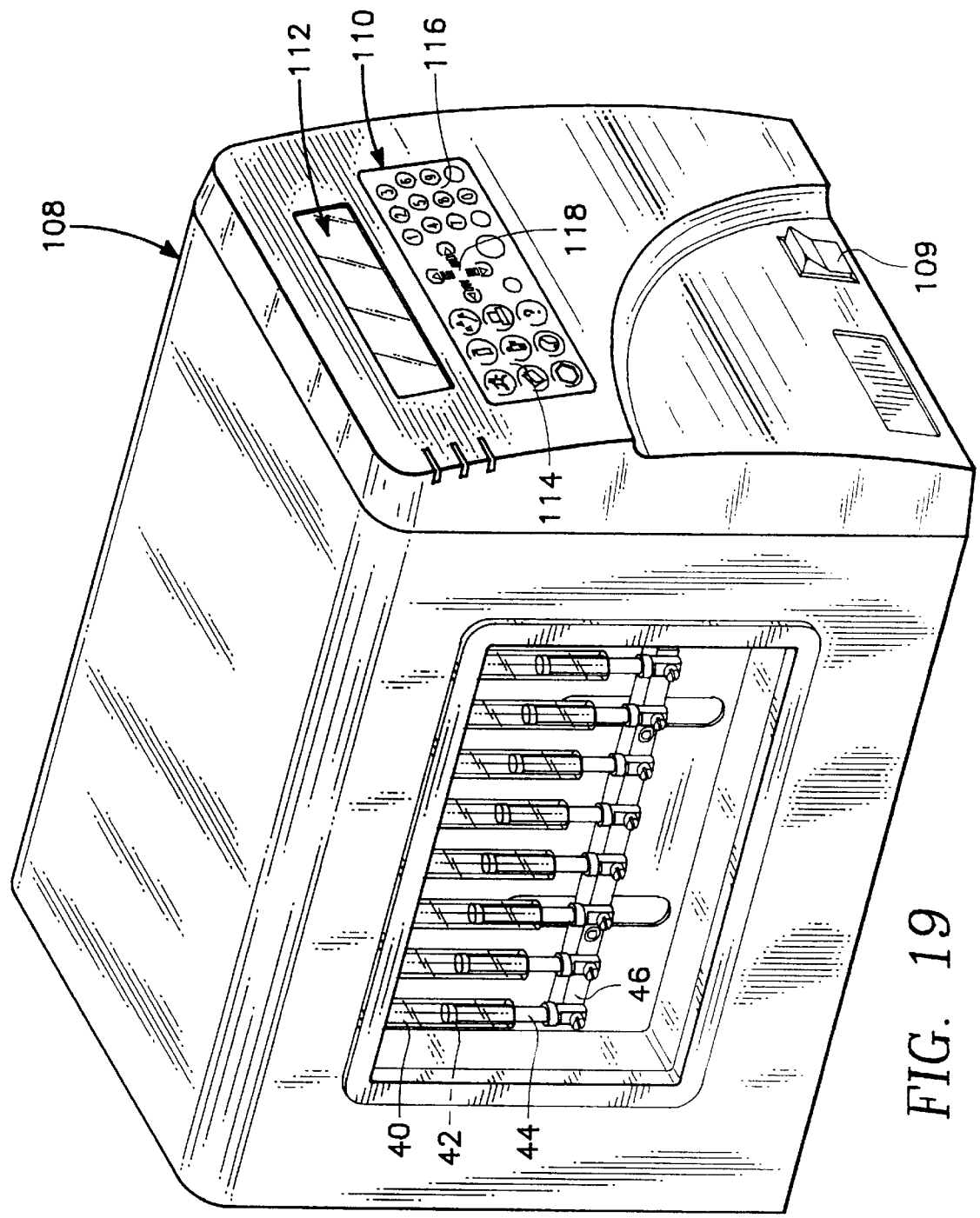
FIG. 19 is an exterior view of the dissolution test apparatus of this invention.

Referring particularly to FIG. 19, there is shown an exterior housing 108 within which the MAXIMIZER embodiment could be located. Mounted on the housing 108 is an icon screen 110. On the icon screen 110 are a plurality of icons 114, numeral buttons 116 and mouse pad 118. By the user physically contacting the appropriate icons 114 in the correct sequence, a certain program can be initiated within the MAXIMIZER embodiment of this invention. The housing 108 includes an on/off switch 109.

What is claimed is:

1. A dissolution sampling aparatus comprising:

a bath containing a liquid;

at least one flask partly submerged in said liquid of said bath, said flask is to contain a media within which is deposited a drug in pill form;

extraction means capable of simultaneously removing a series of aliquots from said media;

valve means located between said flask and said extraction means, said valve means being operable to permit extraction of each said aliquot and depositing of each said aliquot in a deposit location; and valve means comprising a valve housing which has a first port and a second port and a third port, a diaphragm mounted within said valve housing, said diaphragm, when at rest, being positioned to close said first port and said second port and said third port, during said extraction of said aliquot said diaphragm being moved so said first port is open and connecting with said second port with said third port is closed by said diaphragm, during depositing of said aliquot said first port being closed by said diaphragm and said diaphragm being moved so said second port will be open connecting with said third port.

2. The dissolution sampling apparatus as defined in claim 1 wherein:

said extraction means comprising a syringe which includes a piston movably mounted within a syringe body, said piston being connected to a motor, said motor to be operable to cause lineal movement of said piston within said syringe body.

3. The dissolution sampling apparatus as defined in claim 1 wherein:

said deposit location comprising a collection module which has a plurality of vials, each said aliquot is to be deposited within a separate said vial.

4. The dissolution sampling apparatus as defined in claim 3 wherein:

media replacement means for diluting said aliquots contained within said vials.

5. The dissolution sampling apparatus as defined in claim 1 wherein:

a spectrophotometer included within said dissolution sampling apparatus, said spectrophotometer to receive each said aliquot prior to being deposited within said deposit location.

6. A dissolution sampling apparatus comprising:

a bath containing a liquid;

at least one flask partly submerged in said liquid of said bath, said flask is to contain a media within which is deposited a drug in pill form;

extraction means capable of simultaneously removing a series of aliquots from said media;

valve means located between said flask and said extraction means, said valve means being operable to permit extraction of each said aliquot and depositing of each said aliquot in a deposit location;

there being a plurality of said flasks; and there being a second bath included within said dissolution sampling apparatus, said second bath including a plurality of flasks.

7. The dissolution sampling apparatus as defined in claim 6 wherein:

there being a third bath included within said dissolution sampling apparatus, said third bath including a plurality of flasks.

8. A dissolution sampling apparatus comprising:

a bath containing a liquid;

at least one flask partly submerged in said liquid of said bath, said flask is to contain a media within which is deposited a drug in pill form;

extraction means capable of simultaneously removing a series of aliquots from said media;

valve means located between said flask and said extraction means, said valve means being operable to permit extraction of each said aliquot and depositing of each said aliquot in a deposit location; and said deposit location comprising a collection module which has a plurality of vials, each said aliquot is to be deposited within a separate said vial.

* * * * *